US008842282B2

(12) United States Patent
Keller et al.

(10) Patent No.: US 8,842,282 B2
(45) Date of Patent: Sep. 23, 2014

(54) OPTICAL REFLECTORS FOR SPECTROMETER GAS CELLS

(71) Applicants: Lutz Keller, Fontana, CA (US); Alfred Feitisch, Los Gatos, CA (US); Peter Scott, Glendora, CA (US); Mathias Schrempel, Alta Loma, CA (US); Nathan St. John, Rancho Cucamonga, CA (US)

(72) Inventors: Lutz Keller, Fontana, CA (US); Alfred Feitisch, Los Gatos, CA (US); Peter Scott, Glendora, CA (US); Mathias Schrempel, Alta Loma, CA (US); Nathan St. John, Rancho Cucamonga, CA (US)

(73) Assignee: Spectrasensors, Inc., Rancho Cucamonga, CA (US)

( * ) Notice: Subject to any disclaimer, the term of this patent is extended or adjusted under 35 U.S.C. 154(b) by 0 days.

(21) Appl. No.: 13/712,923

(22) Filed: Dec. 12, 2012

(65) Prior Publication Data

US 2014/0160474 A1    Jun. 12, 2014

(51) Int. Cl.
*G01N 21/00* (2006.01)
*G01J 3/28* (2006.01)
*G01N 21/35* (2014.01)
*G01J 3/42* (2006.01)
*G01N 21/03* (2006.01)
*G01N 21/09* (2006.01)

(52) U.S. Cl.
CPC ........ *G01N 21/0303* (2013.01); *G01N 21/3504* (2013.01); *G01J 3/42* (2013.01); *G01N 21/031* (2013.01); *G01N 21/09* (2013.01)
USPC .......................... 356/437; 356/433; 356/326

(58) Field of Classification Search
CPC ........................ G01N 21/3504; G01N 21/031; G01N 21/0303; G01J 3/42
USPC .......................... 356/432–443, 326
See application file for complete search history.

(56) References Cited

U.S. PATENT DOCUMENTS 5,502,308 A * 3/1996 Wong .................. 250/338.5
5,786,893 A * 7/1998 Fink et al. .................. 356/301
(Continued)

FOREIGN PATENT DOCUMENTS

| WO | WO-94/18546 A1 | 8/1994 |
| WO | WO-97/49983 A1 | 12/1997 |
| WO | WO-2008/092114 A2 | 7/2008 |
| WO | WO-2012/054095 A1 | 4/2012 |

OTHER PUBLICATIONS

International Search Report and Written Opinion issued in International Application No. PCT/US2013/074749, mailed Apr. 30, 2014.

*Primary Examiner* — Sang Nguyen
(74) *Attorney, Agent, or Firm* — Mintz Levin Cohn Ferris Glovsky and Popeo, P.C.

(57) ABSTRACT

A spectrometer cell can include a spacer, at least one end cap, and at least one mirror with a reflective surface. The end cap can be positioned proximate to a first contact end of the spacer such that the end cap and spacer at least partially enclose an internal volume of the spectrometer cell. The mirror can be secured in place by a mechanical attachment that includes attachment materials that are chemically inert to at least one reactive gas compound. The mechanical attachment can hold an optical axis of the reflective surface in a fixed orientation relative to other components of the spectrometer cell and or a spectrometer device that comprises the spectrometer cell. The mirror can optionally be constructed of a material such as stainless steel, ceramic, or the like. Related methods, articles of manufacture, systems, and the like are described.

23 Claims, 5 Drawing Sheets

(56) References Cited

U.S. PATENT DOCUMENTS

| | | | |
|---|---|---|---|
| 6,294,389 B1 * | 9/2001 | Vitale et al. | 436/57 |
| 6,486,474 B1 * | 11/2002 | Owen et al. | 250/339.02 |
| 7,288,770 B2 * | 10/2007 | Gamiles et al. | 250/372 |
| 7,352,464 B2 * | 4/2008 | Chen et al. | 356/437 |
| 8,018,981 B2 * | 9/2011 | Eckles et al. | 372/99 |
| 8,299,433 B2 * | 10/2012 | Majewski et al. | 250/338.1 |
| 2007/0081162 A1 * | 4/2007 | Roller et al. | 356/437 |
| 2012/0156368 A1 | 6/2012 | Auth | |
| 2013/0003045 A1 * | 1/2013 | Wilkins | 356/51 |

* cited by examiner

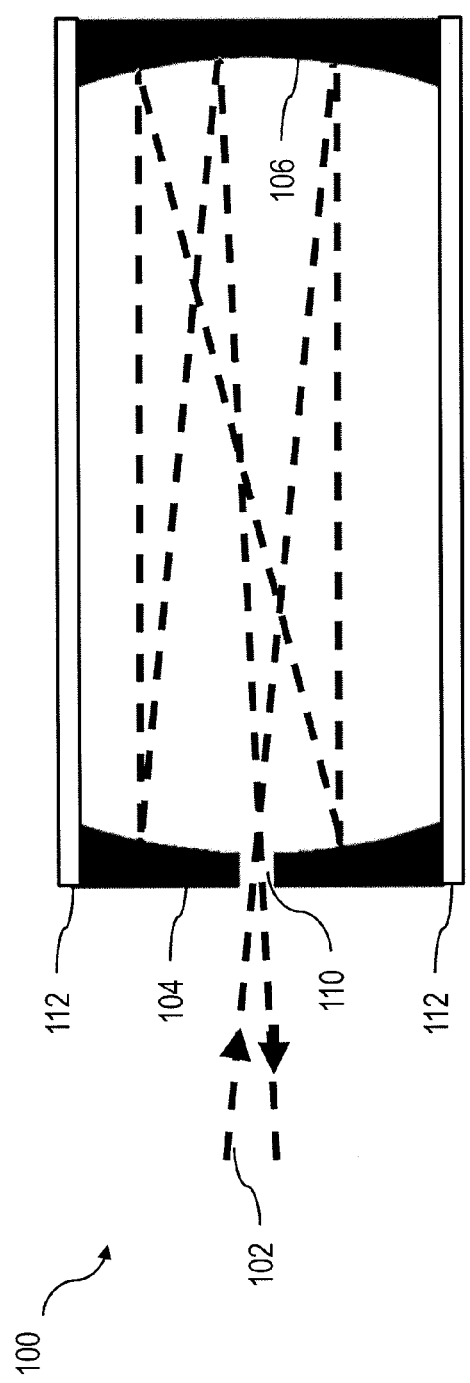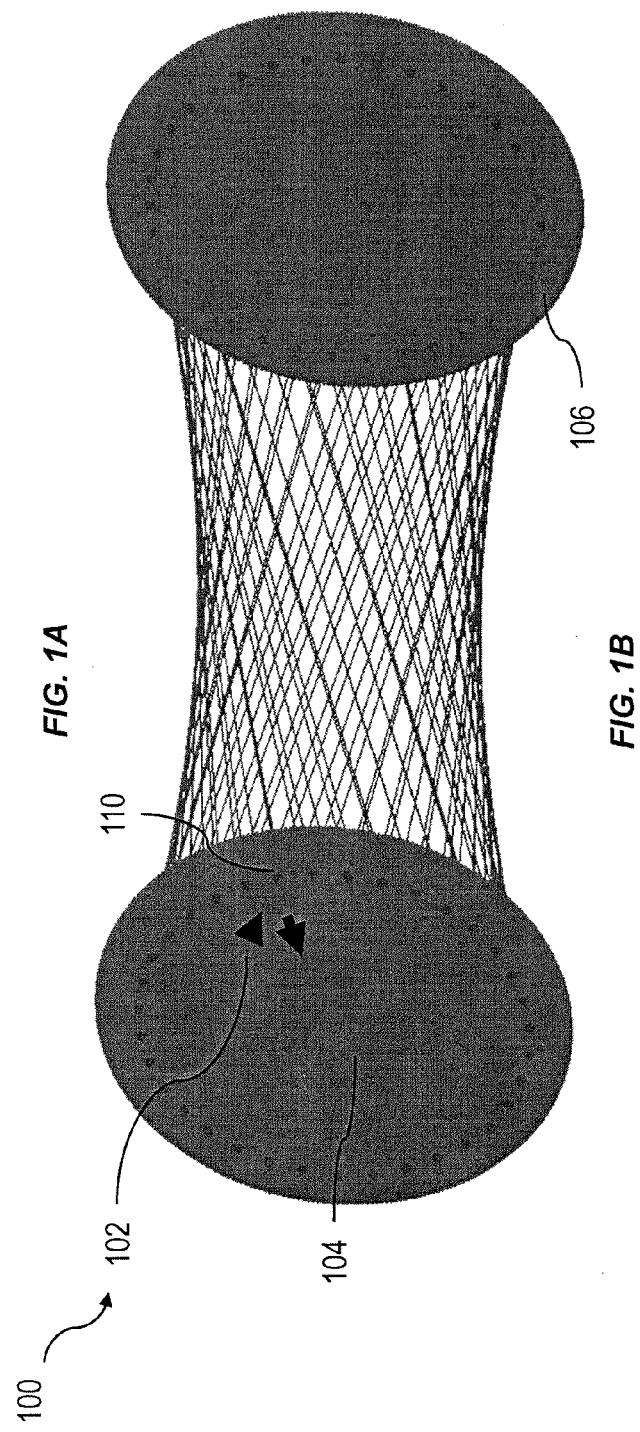
FIG. 1A
FIG. 1B

US 8,842,282 B2

OPTICAL REFLECTORS FOR SPECTROMETER GAS CELLS

TECHNICAL FIELD

The subject matter described herein relates generally to optical reflectors, and more particularly in at least some implementations to optical reflectors usable in spectroscopic instruments for analysis of gas mixtures.

BACKGROUND

Spectroscopic analyzers and other instruments or equipment that rely upon measurements of absorption or emission of light (herein referred to generally as "spectrometers") can be used in a broad range of applications for determining the presence and amount of one or more target analytes in a gas volume or flowing gas stream. Some spectrometers include a spectrometer cell, which can generally feature one or more optical components (e.g. windows or mirrors) for admitting light from one or more light sources and directing this light at least once through a sample of the gas prior to the light reaching a detector for quantifying absorbance, fluorescence or other emission, or the like resulting from interaction of the light with components of the gas sample.

In some applications, a gas volume or flowing gas stream being analyzed by a spectrometer can include chemically reactive compounds, which have the potential to interact in undesirable ways with various components of the spectrometer cell. In particular, optical materials and the optical coatings often used with optical materials in creating windows or mirrors for passing or reflecting light into a sample gas can be quite sensitive to contamination. As an example, optical materials and their optical coatings may be exposed to one or more of acidic and basic gases, liquids, chlorinated compounds, fluorinated compounds, high molecular weight compounds (which therefore typically have relatively low vapor pressures and a tendency to condense onto surfaces), etc., which can alter, influence, or otherwise affect the optical performance of such materials, potentially resulting in false or otherwise flawed spectroscopic analyses.

In addition, currently available sample cell configurations for use in spectrometers are generally not compatible with applications requiring operation over a wide range of temperatures. In particular with multi-pass sample cells that include one or more reflective optical elements, such as for example mirrors or the like, positioned to cause one or more beams of light generated by one or more light sources to be reflected within the sample cell (e.g. to increase a path length over which the one or more light beams travel within a gas sample contained within the sample cell), changes in temperature can require realignment of the reflective optical elements at the operating conditions.

SUMMARY

The current subject matter can provide various advantages over previously available approaches to construction of a spectrometer cell. In one aspect, a spectrometer cell having an internal volume for containing a sample gas includes a spacer, an end cap, and a mirror. The spacer at least partially defines the internal volume and includes a first contact end. The end cap is positioned proximate to the first contact end and also at least partially encloses the internal volume. The mirror includes a reflective surface for receiving and redirecting a beam of light at least once along an optical path length that originates from at least one light source. The optical path length passes at least once through the internal volume. The mirror is secured in place by a mechanical attachment that includes attachment materials that are chemically inert to at least one reactive gas compound. The mechanical attachment holds the optical axis in a fixed orientation relative to other components of the spectrometer cell and of a spectrometer device that comprises the spectrometer cell.

In another aspect, a spectrometer includes an end cap that includes an inner face recessed within a spacer structure. The spacer structure and the inner face at least partially define the internal volume of the spectrometer cell. A mirror can include a reflective surface for receiving and redirecting a beam of light at least once along an optical path length that originates from at least one light source. The reflective surface has an optical axis, and the optical path length passes at least once through the internal volume. The mirror is secured in place on the inner face by a mechanical attachment that includes attachment materials that are chemically inert to at least one reactive gas compound. The mechanical attachment holds the optical axis in a fixed orientation relative to other components of the spectrometer cell and of a spectrometer device that comprises the spectrometer cell.

In another interrelated aspect, a method includes defining, at least partially, an internal volume of a spectrometer cell with a spacer, further enclosing the internal volume with an end cap connected to the first contact end, and receiving and redirecting a beam of light at least once along an optical path length that originates from at least one light source. The spacer includes a first contact end. The optical path length passes at least once through the internal volume. The receiving and redirecting occurs at a mirror that includes a reflective surface having an optical axis and being secured in place by a mechanical attachment that includes attachment materials that are chemically inert to at least one reactive gas compound. The mechanical attachment holds the optical axis in a fixed orientation relative to other components of the spectrometer cell and of a spectrometer device that comprises the spectrometer cell.

In some variations one or more of the following can optionally be included in any feasible combination. The reflective surface can include multiple (e.g. two or more) reflective features, which can have different curvatures. The spacer piece and at least one of the end cap and the mirror can have a similar thermal expansion coefficient. The reflective surface can be formed of a material including at least one of stainless and ceramic. The mirror can further include one or more additional reflective coatings on the reflective surface. The at least one reactive gas compound can include at least one of an acid gas compound, a basic gas compound, a fluorinated compound, and a chlorinated gas compound. The reflective surface can have a surface roughness in one or more of the following ranges: less than approximately 10 Å rms, approximately 10 Å rms to approximately 25 Å rms, approximately 25 Å rms to approximately 50 Å rms, approximately 50 Å rms to approximately 100 Å rms, approximately 100 Å rms to approximately 250 Å rms, and approximately 250 Å rms to approximately 500 Å rms. The reflective surface can include at least one of a planar surface, a spherical curvature, and a parabolic curvature and optionally two or more of such surface shapes.

The reflective surface can be integral to an inner face of the end cap. The inner face can be directed inward toward the internal volume. The mechanical attachment can include a direct and stable physical contact between the end cap and the spacer secured by at least one attachment device. The direct and stable physical contact can ensure at least one of a reproducible alignment and a reproducible orientation of the optical axis relative to the beam of light when the spacer and the end cap are assembled.

The reflective surface can alternatively be disposed on a detachable mirror part. The detachable mirror part can be mechanically connectable to a face of the end cap. The detachable part and an inner face of the end cap can have mating reference surfaces that ensure at least one of a specific alignment and a specific orientation of the optical axis relative to the beam of light when the detachable mirror part and the end cap are joined and the end cap is assembled to the spacer and a direct and stable physical contact between the end cap and the spacer is secured by at least one attachment device.

An inner spacer can be disposed within the internal volume. The inner spacer can have a contact end. The mirror can include a mirror piece that is not directly attached to the end cap. The mirror piece can include a front contact surface on a same side of the mirror piece as the reflective surface and a rear contact surface opposite the front contact surface. The mirror piece can be disposed proximate an inner face of the end cap such that the inner face contacts the rear contact surface and the contact end of the inner spacer contacts the front contact surface to thereby hold the mirror piece secure such that at least one of a reproducible alignment and a reproducible orientation of the optical axis relative to the beam of light are ensured when the spacer, the inner spacer, the mirror piece, and the end cap are assembled.

An apparatus, which can in some implementations be a spectrometer, such as for example a tunable diode laser absorption spectrometer, can include a spectrometer cell including one or more of the features described herein. Such an apparatus can optionally further include one or more light sources for generating one or more light beams, a detector that quantifies a received intensity of light emitted from the light source along a path length, and at least one processor that performs operations comprising controlling a driving current to the laser source and receiving intensity data from the detector. The at least one processor can optionally cause the laser source to provide light having a wavelength modulation frequency and can demodulate the intensity data received from the detector to perform a harmonic spectroscopy analysis method. The at least one processor can mathematically correct a measurement spectrum to account for absorption by compounds in a sample gas through which the light passes. In some examples, the mathematical correction can include subtraction of a reference spectrum from the measurement spectrum where the reference spectrum is collected for a sample of the sample gas in which a concentration of a target analyte has been reduced, for example as part of a differential absorption spectroscopy approach.

The details of one or more variations of the subject matter described herein are set forth in the accompanying drawings and the description below. Other features and advantages of the subject matter described herein will be apparent from the description and drawings, and from the claims.

DESCRIPTION OF DRAWINGS

The accompanying drawings, which are incorporated in and constitute a part of this specification, show certain aspects of the subject matter disclosed herein and, together with the description, help explain some of the principles associated with the disclosed implementations. In the drawings, FIG. 1A and FIG. 1B show diagrams illustrating a cross sectional and a partial cutaway elevation view, respectively, of an example of a multi-pass spectrometer cell;

When practical, similar reference numbers denote similar structures, features, or elements.

DETAILED DESCRIPTION

Figure 2:
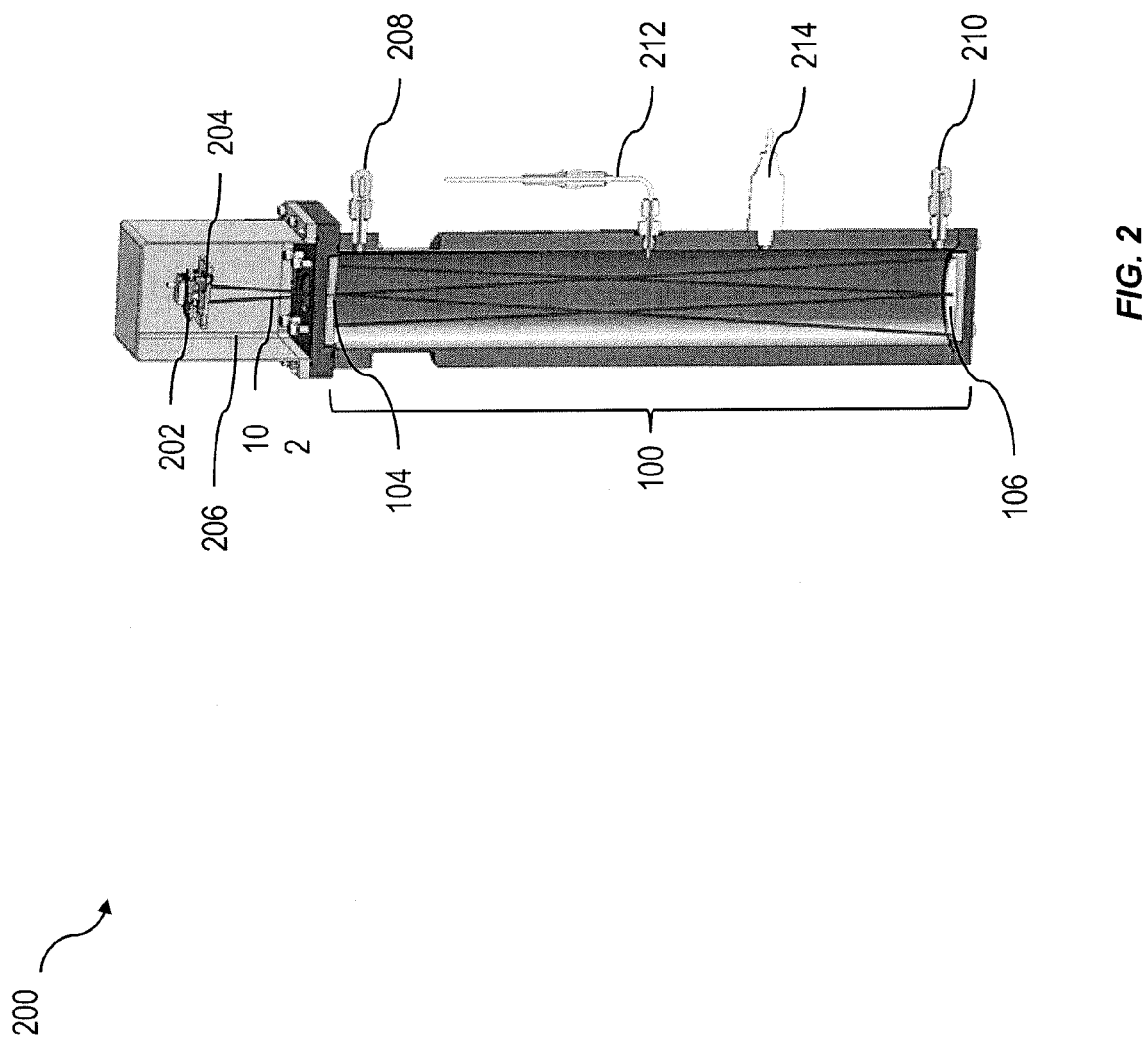
FIG. 2 shows a diagram illustrating a partial cutaway elevation view of an example of a multi-pass spectrometer cell consistent with implementations of the current subject matter.

One example of a multi-pass spectrometer cell is a Herriott cell, in which a mirror is positioned at each end of a cylindrical or otherwise closed gas volume. Such mirrors include a reflective surface for receiving and redirecting a beam of light at least once along an optical path length that originates from one or more light sources. FIG. 1A and FIG. 1B respectively show a cross-section and a partially cutaway elevation view of an example Herriott cell 100. One or more beams of light 102 generated by the one or more light sources (not shown) can be delivered to the space between the two mirrors 104, 106, for example through a hole, window, or port 110 in one of the mirrors 104. The one or more beams of light can be reflected multiple times, optionally at least once, between the mirrors 104, 106 such that an extended spectroscopic path length is created within a relatively compact volume of gas. The two mirrors can be held at a desired distance from each other by one or more structural components of the spectrometer cell 100. For example, as shown in FIG. 1A, a spacer 112 can be disposed to provide a structural support between the two mirrors 104, 106. The elevation view of FIG. 1B shows the Herriot cell 100 with the spacer 112 removed such that the complex path length of the one or more light beams reflecting between two cylindrical mirrors 104, 106 is visible.

A conventional mirror for use in a spectrometer cell, including but not limited to a Herriott cell, can suffer from difficulties in keeping the mirror surface clean, for example in an analytical environment in which process upsets, background gas contamination, or the like can occur. Additionally, as noted above, conventional mirrors, which are generally made of glass, often have a different thermal expansion coefficient relative to other materials (e.g. stainless steel, aluminum, other metals, ceramics, or the like), which are commonly used for forming structural elements (e.g. the spacer 112) of a spectrometer cell. A mirror having different thermal expansion properties compared to the structural components of a spectrometer cell can lead to optical misalignment issues if the spectroscopic cell is used at an operating temperature that differs significantly from a temperature at which the spectrometer cell was assembled and originally aligned. Additionally, because of the relative fragility of glass and glass-like materials, a glass mirror generally cannot be directly mechanically attached (for example using screws, bolts, compression fittings, mechanical clamps, or the like) to structural or flow path parts of a spectrometer cell. Rather, in conventional spectrometers, a glass mirror is typically mounted to a support formed out of a structural material, such as metal or another material, using a flexible adhesive material, such as for example room temperature vulcanizing (RTV) silicone. The support is then mechanically attached to other structural features of the spectrometer cell and the alignment of the mirror with other optical components, a light source, a detector, etc. of the spectrometer is set, usually under factory conditions with very exacting tolerances.

Many flexible adhesives typically used in spectrometer cells are not compatible with one or more reactive gas mixtures. For example, chlorinated compounds present in a gas sample can tend to chemically attack RTV silicone. The resulting reactions can have undesirable effects in either weakening the RTV silicone, thereby potentially causing a loss of structural integrity of the mirror mounting, or releasing gas-phase reaction by-products into the gas sample being analyzed, thereby potentially altering a spectrometer reading relative to the actual composition of the gas sample absent such contamination. Flexible adhesives (e.g. RTV silicone) generally used in mirror mounting in conventional spectrometers can also present difficulties with high temperature operation (e.g. above approximately 120° C., above approximately 200° C., etc.) in that these materials generally have poor thermal stability at elevated temperatures.

Elevated operating temperatures can be important for analytical applications in streams containing ammonia ($NH_3$), hydrogen sulfide ($H_2S$) and other compounds of potential interest. In sulfur recovery unit emissions control, for example, the gas stream can typically be held above at least 120° C. to prevent formation of sulfides, which would artificially which would falsify the emissions measurement (per U.S. Environmental Protection Agency regulations). Other potential high temperature spectroscopy applications can include $H_2S$ measurement in a Claus unit, which removes sulfur compounds from petrochemical streams. Gas streams in such processes can typically be at temperatures in excess of approximately 180° C. to prevent condensation and sublimation of elemental sulfur. Quantification of motor emissions on motor test beds are another potential application of high temperature spectroscopy for which implementations of the current subject matter can resolve potential issues with conventional, currently available spectroscopic approaches. With ever tightening emissions reduction requirements, tunable diode laser (TDL) spectrometric analyzers can be being used to analyze motor exhaust. Due to the temperature constraints of conventional spectrometers, the exhaust gas typically has to be cooled down prior to analysis. A high temperature sample cell TDL measurement can be used to improve the quantitative measurement, avoiding uncertainties related to dissolution of emitted gases in condensed water, which can be a large component of internal combustion engine exhaust.

Implementations of the current subject matter can resolve one or more weaknesses in currently available spectrometer cell configurations and approaches, for example by providing a spectrometer cell usable in a spectrometer that can eliminate or at least reduce the effects of chemically reactive compounds on mirrors and elements of the spectrometer cell associated with mounting and securing of such mirrors to other components of the spectrometer cell. This effect can be achieved through the use of a mechanical attachment that secures the mirror in place using attachment materials that are chemically inert to at least one reactive gas compound. In various examples, the at least one reactive gas compound can include at least one of an acid gas compound, a basic gas compound, a fluorinated compound, and a chlorinated gas compound. Other reactive gas compounds can also be of concern, and the attachment materials can be inert to such other reactive gas compounds as well.

In this manner, the occurrence of potentially false or otherwise flawed spectroscopic results can be mitigated, and a useful lifetime of a spectrometer can be extended. Additionally, mirrors can be constructed of materials that are closely matched in terms of thermal expansion properties to spacers and other structural components of the spectrometer cell. Such a spectrometer cell can be effectively or at least approximately athermal and may not require realignment of the mirrors at any operating temperature or at least over a range of expected operating temperatures. A further advantage that can be realized in conjunction with implementations of the current subject matter can include an improved ability to clean a mirror of a spectrometer cell without requiring a factory recalibration of the spectrometer cell.

In some implementations of the current subject matter, a spectrometer cell can include a reflective surface of a material that differs from materials conventionally used on optical components for spectrometers and other analytical equipment based on optical measurements. Mirrors consistent with implementations of the current subject matter can be formed out of one or more materials, which can advantageously be chemically resistant to attack by compounds expected to be present in a sample gas. For example, instead of glass or the like, a reflector, referred to herein generically as a mirror, can be formed of a polished metal surface, a polished metal surface with one or more additional reflective coatings applied thereto, a polished ceramic surface, a polished ceramic surface with one or more additional reflective coatings applied thereto, or the like.

Bulk materials that can be used in mirrors consistent with implementations of the current subject matter can include stainless steel, for example 316 stainless steel or 320 stainless steel; ceramics, such as for example silica nitride, alumina, or the like; etc. Examples of additional reflective coatings that can be applied consistent with implementations of the current subject matter can include, but are not limited to at least one of a metal and a dielectric material for enhancing reflectively of the mirror surface. Metals that can be used as reflective coatings can include gold, silver, aluminum, other metals, two or more metals in combination, and the like.

Because metals and ceramics and other materials consistent with the implementations described generally can have mechanical properties consistent with directly connecting components formed of such materials to other structural components of a spectrometer cell, a mirror formed of one or more of these materials can be secured within a spectrometer cell assembly without the need for a flexible adhesive, such as for example RTV silicone or the like. In other words, the mechanical attachment can secure the mirror in place such that an optical axis of the reflective surface (e.g. an axis that passes through the center of curvature of the reflective surface of the mirror and generally coincides with the axis of rotational symmetry of the reflective surface) is held in a fixed and reproducible orientation relative to other components of the spectrometer cell and of a spectrometer device that comprises the spectrometer cell.

A directly mechanical attachment of a mirror component of a spectrometer cell to one or more other structural components of the spectrometer cell can be very useful for a variety of reasons. For example, a mirror mounted in a conventional manner using a flexible adhesive or other mounting approach that does not result in a positive solid on solid contact can require fine tuning or other calibration and alignment in a factory or other controlled service setting to ensure that the one or more beams of light are reflected along a desired axis to thereby impinge upon the detector. The alignment process can be quite delicate because of the high tolerances required to properly align one or more beams of light that can in some implementations be reflected numerous times before reaching the detector. As such, if a spectrometer cell is exposed to a process upset that results in deposition of one or more condensed-phase (e.g. liquid, solid, adsorbed, chemisorbed, etc.) contaminants on a reflective surface of a mirror, or if the background constituents of a gas sample being analyzed contain compounds with a sufficiently low vapor pressure or high reactivity that they tend to accumulate on the mirror surfaces, cleaning of the mirror surfaces can be a non-trivial exercise that often cannot be performed in the field. One example of this problem can arise in a spectrometer used in monitoring natural gas, hydrocarbon streams, refining operations, or the light can be exposed to a variety of relatively low vapor pressure compounds, which can tend to condense on mirror surfaces.

An inability to clean a mirror in a spectrometer cell in the field (or otherwise without returning the entire spectrometer or spectrometer cell to a calibration facility can result in one or more of excessive downtime while the spectrometer is removed from service to be cleaned and re-calibrated either at the factory or in another controlled setting, less than optimal performance as the period between such cleanings and re-calibrations is extended to reduce the fractional downtime of the analytical system, or the like.

Implementations of the current subject matter that include a mirror that can be directly and securely mechanically attached to one or more other structural components of a spectrometer cell can overcome these difficulties. Such a mirror can be removed from the spectrometer cell, cleaned using one or more approaches (e.g. wiping, polishing, immersion in one or more solvents, ultrasonic cleaning, or the like), and then returned to the spectrometer cell in the field. Because a direct and stable physical contact exists between such a mirror and the other spectrometer cell components, concerns about alignment errors upon reinstallation of the removed mirror can be significantly reduced.

In another example of a spectrometer 200 shown in FIG. 2, one or more mirrors 104, 106 having one or more reflective mirror surfaces, which can be curved (e.g. spherical, parabolic, having a spatially varying curvature, etc.) or flat (e.g. planar), can be supported or anchored to one or more structural elements of a spectrometer cell 100. A reflective surface can optionally include two or more type of curvature, such as for example a spherical mirror having one or more planar facets. FIG. 2 shows a spectrometer 200 including a spectrometer cell 100 through which light 102 from a light source 202 is reflected multiple times between two mirrors 104, 106 before reaching a detector 204. The light source 202 and the detector can optionally be contained within a head unit 206, which can optionally include temperature control, electronics to control the light source (e.g. a laser) and receive signals from the detector, etc. A gas sample can flow into the spectrometer cell 100 via a gas inlet 208 and pass out of the spectrometer cell 100 via a gas outlet 210. One or more of a temperature sensor 212, a pressure sensor 214, or other sensing devices (not shown) can be included to monitor conditions within the spectrometer cell 100.

Figure 3:
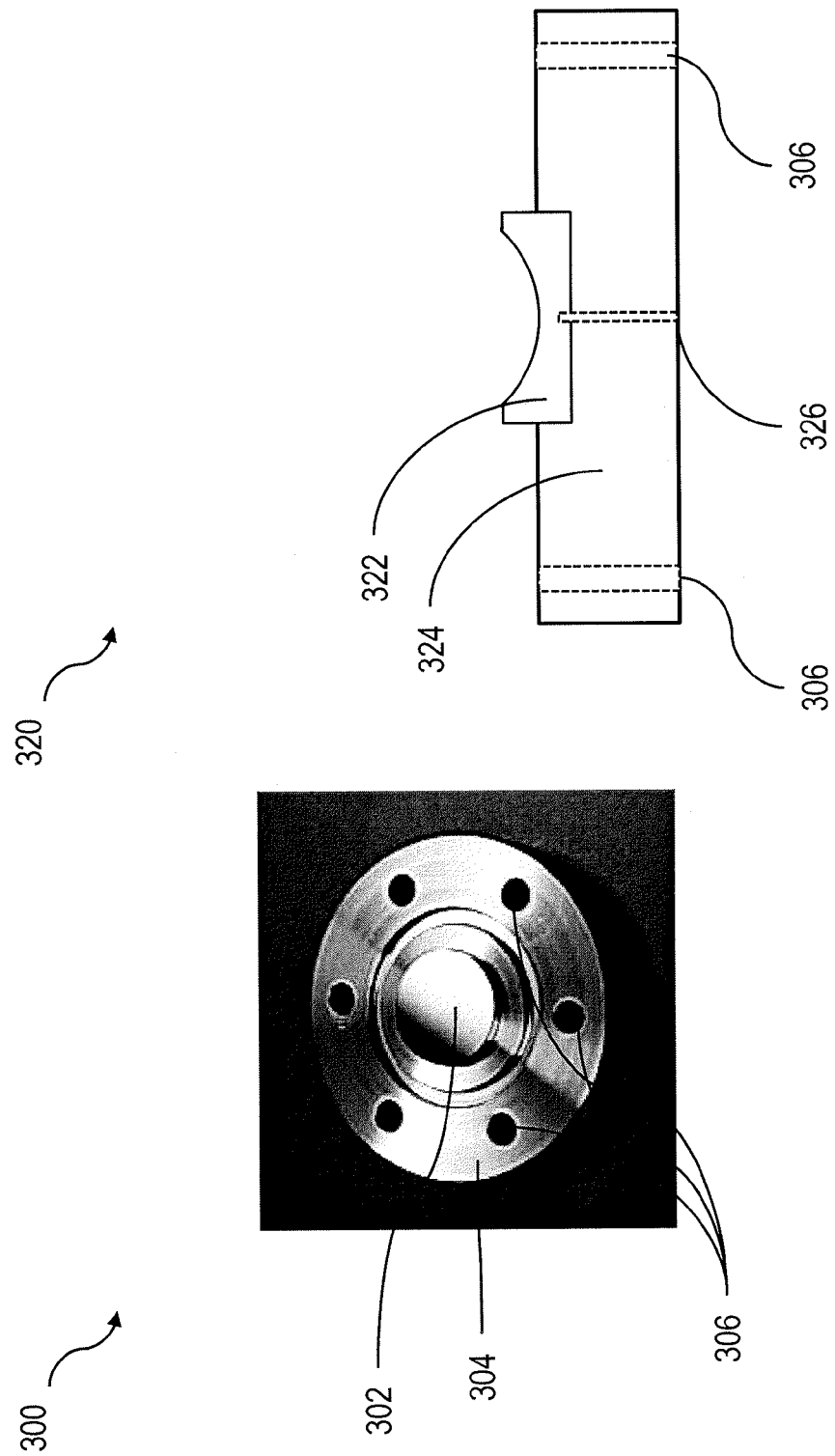
FIG. 3A and FIG. 3B show diagrams illustrating a top and a side view, respectively, of end caps usable in a spectrometer cell consistent with implementations of the current subject matter.

FIG. 3A and FIG. 3B shows two approaches consistent with implementations of the current subject matter relating to configurations of mirrors or mirror surfaces usable in a spectrometer cell 100. It will be understood that one or more mirrors used in a spectrometer cell 100 consistent with implementations of the current subject matter can include one or more features similar to those described and shown.

In FIG. 3A, which shows an elevation view of a spectrometer component 300, a mirror 302 is formed as a contiguous part of an end cap 304 of a spectrometer cell (not shown in FIG. 3A). As shown in FIG. 3A, the reflective surface of the mirror 302 is integral to an inner face of the end cap 304. When assembled as part of a spectrometer cell, the inner face and therefore the reflective surface of the mirror 302 is directed inward toward the internal volume of the spectrometer cell. In this example, the end cap 304 includes machined holes 306 to accept bolts that secure the end cap 304 to a cylindrical spacer component (not shown in FIG. 3A) that maintains a distance between the end cap 304 and another component (which can optionally also include a mirror) positioned at an opposite end of a spectrometer cell. The spacer can also serve to enclose a gas volume through which the light from the light source passes one or more times. The end cap 304 can be machined and then polished along a central axis to form a curved mirror surface that can thereby be aligned to extremely tight tolerances. The end cap 304 is bolted or otherwise secured with one or more attachment devices (e.g. screws, clamps, etc.) directly to a solid mating surface on the spacer component of the spectrometer cell to form a mechanical attachment that includes a direct and stable physical contact between the end cap and the spacer. Accordingly, a fixed orientation of the mirror optical axis can be reproducibly achieved even if the end cap 304 is removed for cleaning, polishing, or other maintenance activities.

In FIG. 3B, which shows a side cross-sectional view of another spectrometer component 320, a separate, detachable mirror part 322 can be removable from an end cap 324. The end cap 324 can be configured to receive the detachable mirror part 322. The detachable mirror part 322 and the end cap 324 can have mating reference surfaces that ensure at least one of a specific alignment and a specific orientation of the optical axis relative to the beam of light when the detachable mirror part 322 and the end cap 324 are assembled. In other words, and to make a positive and solid connection with the mirror 322 such that the alignment of the mirror 322 relative to the end cap 324 and to other structural components of the spectrometer cell (not shown in FIG. 3B) to which the end cap 324 is mechanically secured using one or more attachment devices can be maintained even if the end cap 324 is detached from and reattached to the other structural components of the spectrometer cell or if the detachable mirror piece mirror 322 is removed from and reattached to the end cap 324 on one face of the end cap 324. In the example shown in FIG. 3B, the end cap 324 includes machined holes 306 to accept bolts that secure the end cap 324 to a spacer component (not shown in FIG. 3B) that maintains a distance between the end cap 324 and another component (which can optionally also include a mirror) positioned at an opposite end of a spectrometer cell. The mirror 322 can optionally be positioned in a recess machined into one side or face of the end cap 324. The recess can advantageously be machined to very tight tolerances such that the mirror fits snugly into the recess. More generally, matching reference surfaces on the mirror 322 and the face of the end cap 324 can be machined or otherwise formed to be capable of mating in a manner that ensures a specific alignment and orientation of the mirror 322 relative to the beam of light emitted by the light source. A screw or other mechanical connection can be added, for example through a screw or bolt hole 326 in the opposite side of the end cap 324 from the recess.

The approach of FIG. 3B can in some examples facilitate ease of manufacture in that only the mirror 322 need be polished and have its optical axis aligned with high precision relative to one or more reference surfaces of the mirror 322 (e.g. the back of the mirror 322, a circumference of the mirror 322, etc.) while the end cap 324 need only be machined to the necessary tolerances to be joined with the mirror 322 so that the optical axis is correctly aligned when the spectrometer cell is assembled. For cleaning or other maintenance, the end cap 324 can be removed or otherwise detached other structural components of the spectrometer cell and then reinstalled without the need for additional alignment procedures. Similarly, the mirror 322 can be removed or otherwise detached from the end cap 324. Because of the positive mechanical connection between one or more reference surfaces of the mirror 322 and the end cap 324, accurate alignment can be achieved during one or more disassembly and reassembly procedures without need for a complicated realignment procedure.

In another example configuration that is consistent with one or more implementations of the current subject matter, an end cap can include an inner face recessed within a spacer structure. The spacer structure can be integral to the end cap. In other words, the inner face can optionally be formed as an end of a bore (e.g. a cylindrical bore) into a solid structure such that a hollow area partially defining an internal volume is formed by the walls of the bore and the end of the bore. A mirror or mirror piece consistent with one or more implementations of the current subject matter disclosed herein can be disposed at the end of the bore. For example, the end of the bore can be machined or otherwise formed to a desired reflector surface shape and polished and/or coated with a reflective coating. Alternatively, a separate, detachable mirror piece can be added within the bore and secured at the end of the bore by a mechanical attachment. A mirror consistent with this implementation can have one or more reflective surfaces for receiving and redirecting a beam of light at least once along an optical path length that originates from at least one light source. The one or more reflective surfaces can include at least one optical axis. The mechanical attachment can include attachment materials that are chemically inert to at least one reactive gas compound and can hold the optical axis in a fixed orientation relative to other components of the spectrometer cell and of a spectrometer device that comprises the spectrometer cell.

In some examples, a mirror consistent with one or more implementations of the current subject matter need not be polished to be as smooth as a glass mirror. For example, a mirror for use with a tunable diode laser spectrometer that relies upon harmonic spectroscopy techniques need not achieve as high a degree of reflectivity as a mirror used in a direct absorption method. The ability of a harmonic spectroscopy method to compensate for losses of intensity of light emitted from the one or more light sources can result from the fact that the metric for determining a concentration of an analyte is a ratio of the harmonic signal to the direct absorption signal. Attenuation of the light intensity due to reflectivity losses in the optical path generally affects both the harmonic signal in the direct signal equally. Therefore, a metal mirror as described herein can be ground to a surface roughness parameter that is not necessarily smooth as is typically achieved with a glass mirror. For example, a surface roughness of a mirror consistent with implementations of the current subject matter can optionally be in a range of approximately 10 Å rms (root mean squared) to 500 Å rms. In various implementations of the current subject matter, a surface roughness of the mirror can be approximately 500 Å rms, approximately 250 Å rms, approximately 100 Å rms, approximately 50 Å rms, approximately 25 Å rms, approximately 10 Å rms, or any range including two of these values as its outer limits. Other ranges of surface roughness are also within the scope of the current subject matter.

In some implementations of the current subject matter, a spectrometer cell can be designed to be operable at temperatures in a range of 120° to 180° C. Such a spectrometer cell can be aligned at a first temperature, for example approximately when temperature, and that alignment can remain consistent even at elevated temperatures. In contrast, a conventional spectrometer cell that includes a glass mirror and other structural components that are formed out of the material with a different thermal expansion coefficient than the glass material of the mirror can experience unbalanced thermal expansion at the elevated operating temperature. This unbalanced thermal expansion and caused the alignment, which was established at the assembly temperature, to no longer be valid at a elevated operating temperature. Particularly in a spectrometer cell in which one or more beams of light are reflected numerous times between one or more mirrors or other reflective elements, a small deviation in the shape of the spectrometer so can result in the light beam not impinging or only partially impinging upon the detector. This effect can cause the spectrometer to either not working all or work with a reduced accuracy or potential to introduce significant errors. To address such concerns, implementations of the current subject matter can optionally include a spectrometer cell in which all of the components, including both the spacer and one or more end caps, are formed of the same material or if of different materials of materials with comparable thermal expansion coefficients. A single material used in these components can in some examples be stainless steel, optional including one or more alloys, a ceramic, or other comparable materials. Stainless steel can be particularly advantageous in some implementations because stainless steel is a convenient material for use in making things and other connections to gas tubing that may be used to deliver a gas sample to the volume of the spectrometer cell and to allow such a sample to be vented from the spectrometer cell.

Figure 4:
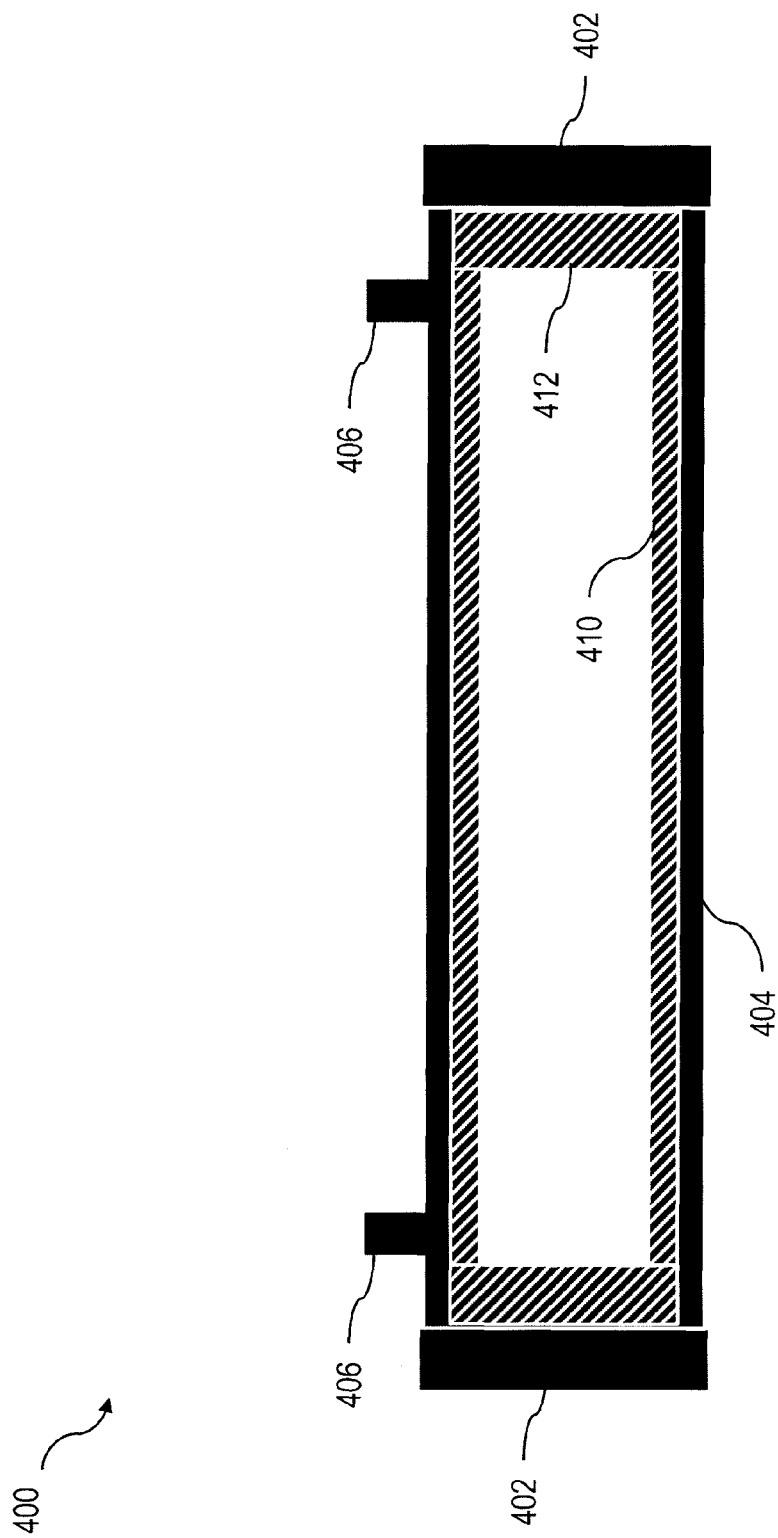
FIG. 4 shows a diagram illustrating a side view of a spectrometer cell consistent with implementations of the current subject matter.

In another, related implementation of the current subject matter, an athermal spectrometer cell can be formed of a two-layer structure, for example as illustrated in FIG. 4. As shown in FIG. 4, consistent with some implementations of the current subject matter, a spectrometer cell 400 can include an outer structure and an inner structure. The outer structure can be formed of one or more structural materials, such as for example stainless steel, ceramic, or the like. As shown in FIG. 4, the outer structure includes at least one, and optionally two, end caps 402 and an outer spacer 404. Gas connections 406, physical support and attachment points, and the like can attach to the outer spacer piece 404. The end caps 402 and the outer spacer piece 404 can be formed of a structurally stable material, such as for example stainless steel, aluminum, ceramic, etc. The inner structure can include one or more mirror pieces 410, which can be positioned near one or both of the end caps 402. The one or more mirror pieces can include a front contact surface on a same side of the mirror piece as a reflective surface and a rear contact surface opposite the front contact surface.

An inner spacer 412 can be included and can have a contact end (or two contact ends as shown in FIG. 4) respectively in contact with one of the one or more mirror pieces 410. In one example, the inner spacer 412 and the one or more mirror pieces 410 can all be formed of a same material, such as for example glass. One or both of the end caps 402 can include at least one optical pass-through to allow entry and/or exit of a light beam as it passes between a light source and a detector. A mirror piece 410 can be disposed proximate an inner face of the corresponding end cap 402 such that the inner face contacts the rear contact surface and the contact end of the inner spacer contacts the front contact surface to thereby hold the mirror piece secure such that at least one of a reproducible alignment and a reproducible orientation of the optical axis of the reflective surface of the mirror relative to the beam of light are ensured when the outer spacer 404, the inner spacer 412, the one or more mirror pieces 410, and the one or more end caps 402 are assembled.

The one or more mirror pieces 410 can optionally be circular and can include an annular registration surface around the outer circular edges. The inner spacer 412 can be cylindrical in shape, with a contact edge located on at least one end of the cylinder for mating with the annular registration surface of a mirror piece 410. In this manner, the one or more mirror pieces 410 can be machined or otherwise formed to a close tolerance and mechanically held in contact with one or more rigid, solid contact surfaces on the inner spacer piece such that alignment of the one or more mirror pieces 410 is ensured through this positive mechanical contact and a flexible adhesive or other securing material is not required. The parts that assemble to create the inner structure can be held in contact with each other (e.g. the annular registration surface of the mirror piece 410 can be held in physical contact with the contact edge located on at least one end of the inner spacer 412) by the outer structure. In an example in which the outer structure is formed of a metal, ceramic, or other material that can be bolted, screwed, or otherwise mechanically connected together, this outer structure can encapsulate, protect, support, and retain the one or more mirror pieces 410 and the inner spacer 412 in contact with each other. Forming of the inner structure from a single type of material or two or more materials having a same thermal or similar expansion coefficient can alleviate issues discussed above in regards to misalignment of the optical path caused by mismatched expansion or contraction under changes in operating temperature of the spectrometer cell.

The inner spacer 412 can, consistent with implementations of the current subject matter, be a cylinder or other shape with a volume at least partially enclosed inside the hollow part of the shape. In other implementations, the inner spacer 412 can be a rod or other solid shape having contact ends that contact with a contact area on each of one or more mirror pieces 410 to create a positive mechanical connection. In some implementations of the current subject matter, the inner space 412 can include two or more pieces that act to stabilize and secure the one or more mirror pieces. For example, an inner spacer 412 can assume a tripod-like configuration, in which three (or two or optionally more than three) rods, each having a contact end that creates a positive mechanical connection with the a contact area on each of one or more mirror pieces 410.

Figure 5:
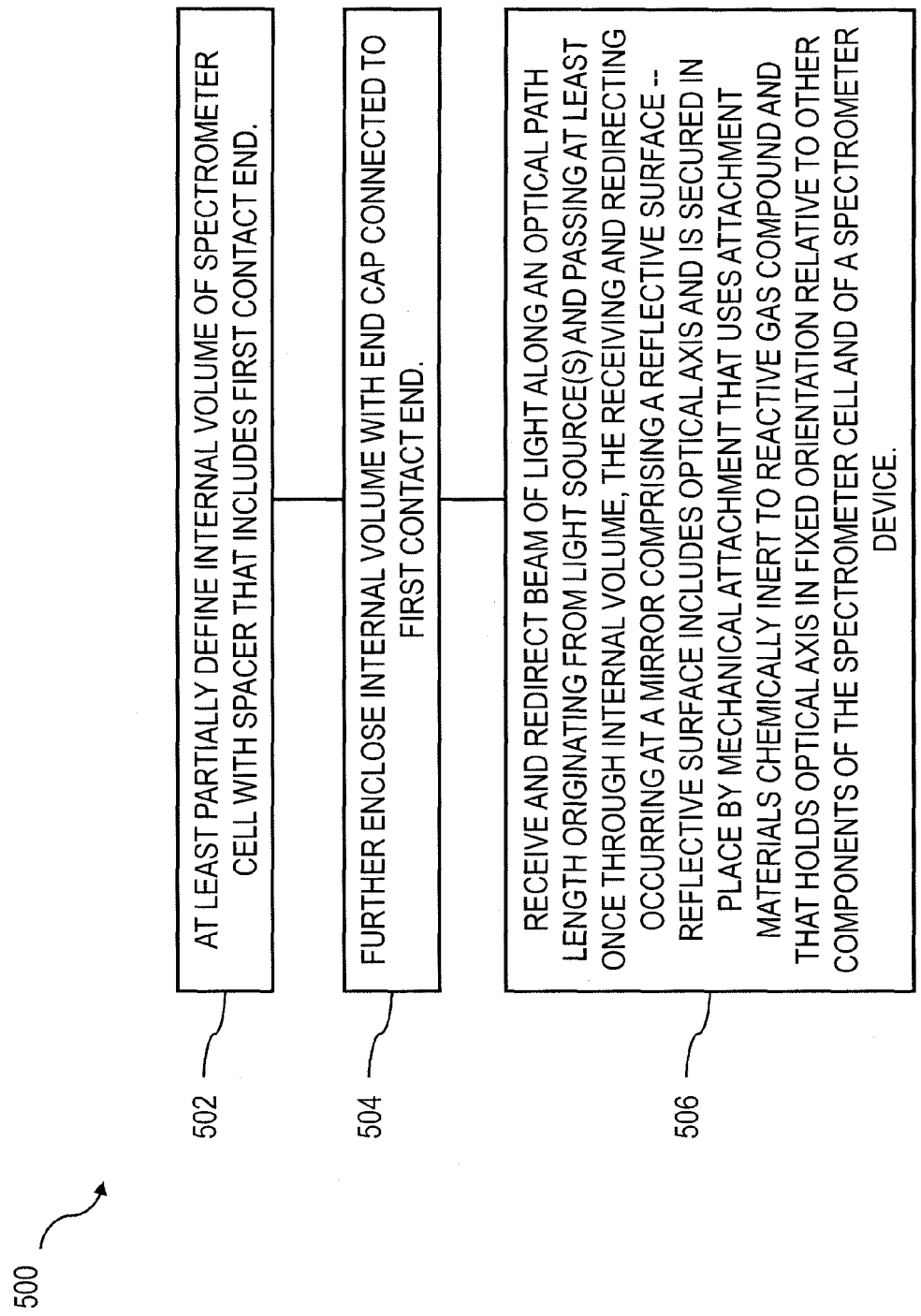
FIG. 5 is a process flow diagram illustrating aspects of a method having one or more features consistent with implementations of the current subject matter.

FIG. 5 shows a process flow chart 500 that illustrates features of a method. Ne or more of these features can be present in various implementations of the current subject matter. At 502, a spacer that includes a first contact end at least partially defines an internal volume of a spectrometer cell is defined. At 504, the internal volume is further enclosed with an end cap connected to the first contact end, and at 506 a beam of light is received and redirected at least once along an optical path length that originates from at least one light source. The optical path length passes at least once through the internal volume. The receiving and redirecting occurs at a mirror that includes a reflective surface having an optical axis and being secured in place by a mechanical attachment comprising attachment materials that are chemically inert to at least one reactive gas compound. The mechanical attachment holds the optical axis in a fixed orientation relative to other components of the spectrometer cell and of a spectrometer device that comprises the spectrometer cell.

The subject matter described herein can be embodied in systems, apparatus, methods, and/or articles depending on the desired configuration. The implementations set forth in the foregoing description do not represent all implementations consistent with the subject matter described herein. Instead, they are merely some examples consistent with aspects related to the described subject matter. Although a few variations have been described in detail above, other modifications or additions are possible. In particular, further features and/or variations can be provided in addition to those set forth herein. For example, the implementations described above can be directed to various combinations and subcombinations of the disclosed features and/or combinations and subcombinations of several further features disclosed above. The specific configuration of a spectrometer cell can take any of a large number of shapes consistent with the subject matter as claimed below. In addition, the logic flows depicted in the accompanying figures and/or described herein do not necessarily require the particular order shown, or sequential order, to achieve desirable results. Other implementations may be within the scope of the following claim.

What is claimed is:

1. A spectrometer cell having an internal volume for containing a sample gas, the spectrometer cell comprising:
a spacer, the spacer at least partially defining the internal volume and comprising a first contact end;
an end cap, the end cap positioned proximate to and contacting the first contact end and at least partially enclosing the internal volume; and
a mirror, the mirror comprising a reflective surface for receiving and redirecting a beam of light at least once along an optical path length that originates from at least one light source, the reflective surface having an optical axis, the optical path length passing at least once through the internal volume, the mirror being secured in place by a mechanical attachment comprising attachment materials that are chemically inert to at least one reactive gas compound, the mechanical attachment holding the optical axis in a fixed orientation relative to other components of the spectrometer cell and of a spectrometer device that comprises the spectrometer cell.

2. A spectrometer cell as in claim 1, wherein the spacer piece and at least one of the end cap and the mirror have a similar thermal expansion coefficient.

3. A spectrometer cell as in claim 1, wherein the reflective surface is formed of a material comprising at least one of stainless steel and ceramic.

4. A spectrometer cell as in claim 1, wherein the mirror further comprises one or more additional reflective coatings on the reflective surface.

5. A spectrometer cell as in claim 1, wherein the at least one reactive gas compound comprises at least one of an acid gas compound, a basic gas compound, a fluorinated compound, and a chlorinated gas compound.

6. A spectrometer cell as in claim 1, wherein the reflective surface has a surface roughness in one or more of the following ranges: less than approximately 10 Å rms, approximately 10 Å rms to approximately 25 Å rms, approximately 25 Å rms to approximately 50 Å rms, approximately 50 Å rms to approximately 100 Å rms, approximately 100 Å rms to approximately 250 Å rms, and approximately 250 Å rms to approximately 500 Å rms.

7. A spectrometer cell as in claim 1, wherein the reflective surface comprises at least one of a planar surface, a spherical curvature, and a parabolic curvature.

8. A spectrometer cell as in claim 1, wherein the reflective surface is integral to an inner face of the end cap, the inner face being directed inward toward the internal volume, and wherein the mechanical attachment comprises a direct and stable physical contact between the end cap and the spacer secured by at least one attachment device, the direct and stable physical contact ensuring at least one of a reproducible alignment and a reproducible orientation of the optical axis relative to the beam of light when the spacer and the end cap are assembled.

9. A spectrometer cell as in claim 1, wherein the reflective surface is disposed on a detachable mirror part, the detachable mirror part being mechanically connectable to a face of the end cap, the detachable part and an inner face of the end cap having mating reference surfaces that ensure at least one of a specific alignment and a specific orientation of the optical axis relative to the beam of light when the detachable mirror part and the end cap are joined and the end cap is assembled to the spacer and a direct and stable physical contact between the end cap and the spacer is secured by at least one attachment device.

10. An spectrometer cell as in claim 1, further comprising an inner spacer disposed within the internal volume, the inner spacer having a contact end, wherein the mirror comprises a mirror piece that is not directly attached to the end cap, the mirror piece comprising a front contact surface on a same side of the mirror piece as the reflective surface and a rear contact surface opposite the front contact surface, the mirror piece being disposed proximate an inner face of the end cap such that the inner face contacts the rear contact surface and the contact end of the inner spacer contacts the front contact surface to thereby hold the mirror piece secure such that at least one of a reproducible alignment and a reproducible orientation of the optical axis relative to the beam of light are ensured when the spacer, the inner spacer, the mirror piece, and the end cap are assembled.

11. An spectrometer cell as in claim 1, further comprising an inner spacer disposed within the internal volume, the inner spacer having a contact end, wherein the mirror comprises a mirror piece that is not directly attached to the end cap, the mirror piece comprising a front contact surface on a same side of the mirror piece as the reflective surface and a rear contact surface opposite the front contact surface, the mirror piece being disposed proximate an inner face of the end cap such that the inner face contacts the rear contact surface and the contact end of the inner spacer contacts the front contact surface to thereby hold the mirror piece secure such that at least one of a reproducible alignment and a reproducible orientation of the optical axis relative to the beam of light are ensured when the spacer, the inner spacer, the mirror piece, and the end cap are assembled.

12. A spectrometer cell as in claim 1, wherein the mechanical attachment comprises a direct and stable physical contact such that the fixed orientation is reproducible when the mirror is removed from and replaced into the spectrometer cell.

13. A spectrometer cell as in claim 1, wherein the direct and stable mechanical attachment does not include a flexible adhesive.

14. A method comprising:
defining, at least partially, an internal volume of a spectrometer cell with a spacer, the spacer comprising a first contact end;
further enclosing the internal volume with an end cap connected to the first contact end; and
receiving and redirecting a beam of light at least once along an optical path length that originates from at least one light source, the optical path length passing at least once through the internal volume, the receiving and redirecting occurring at a mirror comprising a reflective surface, the reflective surface having an optical axis and being secured in place by a mechanical attachment comprising attachment materials that are chemically inert to at least one reactive gas compound, the mechanical attachment holding the optical axis in a fixed orientation relative to other components of the spectrometer cell and of a spectrometer device that comprises the spectrometer cell.

15. A method as in claim 14, wherein the spacer piece and at least one of the end cap and the mirror have a similar thermal expansion coefficient.

16. A method as in claim 15, wherein the at least one reactive gas compound comprises at least one of an acid gas compound, a basic gas compound, a fluorinated compound, and a chlorinated gas compound.

17. A method as in claim 14, wherein the reflective surface is formed of a material comprising at least one of stainless steel and ceramic.

18. A method as in claim 14, wherein the mirror further comprises one or more additional reflective coatings on the reflective surface.

19. A method as in claim 14, wherein the reflective surface has a surface roughness in one or more of the following ranges: less than approximately 10 Å rms, approximately 10 Å rms to approximately 25 Å rms, approximately 25 Å rms to approximately 50 Å rms, approximately 50 Å rms to approximately 100 Å rms, approximately 100 Å rms to approximately 250 Å rms, and approximately 250 Å rms to approximately 500 Å rms.

20. A method as in claim 14, wherein the reflective surface comprises at least one of a planar surface, a spherical curvature, and a parabolic curvature.

21. A method as in claim 14, wherein the reflective surface is integral to an inner face of the end cap, the inner face being directed inward toward the internal volume, and wherein the mechanical attachment comprises a direct and stable physical contact between the end cap and the spacer secured by at least one attachment device, the direct and stable physical contact ensuring at least one of a reproducible alignment and a reproducible orientation of the optical axis relative to the beam of light when the spacer and the end cap are assembled.

22. A method as in claim 14, wherein the reflective surface is disposed on a detachable mirror part, the detachable mirror part being mechanically connectable to a face of the end cap, the detachable part and an inner face of the end cap having mating reference surfaces that ensure at least one of a specific alignment and a specific orientation of the optical axis relative to the beam of light when the detachable mirror part and the end cap are joined and the end cap is assembled to the spacer and a direct and stable physical contact between the end cap and the spacer is secured by at least one attachment device.

23. A spectrometer cell having an internal volume for containing a sample gas, the spectrometer cell comprising:
an end cap, comprising an inner face recessed within a spacer structure, the spacer structure and the inner face at least partially defining the internal volume
a mirror, the mirror comprising a reflective surface for receiving and redirecting a beam of light at least once along an optical path length that originates from at least one light source, the reflective surface having an optical axis, the optical path length passing at least once through the internal volume, the mirror being secured in place on or proximate to the inner face by a mechanical attachment comprising attachment materials that are chemically inert to at least one reactive gas compound, the mechanical attachment holding the optical axis in a fixed orientation relative to other components of the spectrometer cell and of a spectrometer device that comprises the spectrometer cell.

* * * * *